(12) United States Patent
Van Den Berg

(10) Patent No.: US 6,508,273 B1
(45) Date of Patent: Jan. 21, 2003

(54) DEVICE AND METHOD FOR CONTROLLING A LIQUID FLOW

(75) Inventor: Albert Van Den Berg, Nijverdal (NL)

(73) Assignee: Universiteit Twente (Mesa Research Instituut), Enschede (NL)

( * ) Notice: Subject to any disclaimer, the term of this patent is extended or adjusted under 35 U.S.C. 154(b) by 0 days.

(21) Appl. No.: 09/807,320
(22) PCT Filed: Oct. 15, 1999
(86) PCT No.: PCT/NL99/00641
§ 371 (c)(1), (2), (4) Date: Jul. 5, 2001
(87) PCT Pub. No.: WO00/22427
PCT Pub. Date: Apr. 20, 2000

(30) Foreign Application Priority Data

Oct. 15, 1998 (NL) .............................................. 1010327

(51) Int. Cl.⁷ ................................................ F15C 1/04
(52) U.S. Cl. ........................ 137/827; 137/807; 137/833; 204/454; 204/601
(58) Field of Search ................................ 137/827, 833, 137/807; 204/454, 600, 601

(56) References Cited

U.S. PATENT DOCUMENTS

| | | | |
|---|---|---|---|
| 4,859,301 A | * 8/1989 | Brenner et al. | 204/452 |
| 4,908,112 A | * 3/1990 | Pace | 210/198.2 |
| 5,092,972 A | 3/1992 | Ghowsi | 204/182.1 |
| 5,126,022 A | * 6/1992 | Soane et al. | 204/458 |
| 5,282,942 A | 2/1994 | Herrick et al. | 204/183.2 |
| 5,374,834 A | 12/1994 | Geis et al. | 257/239 |
| 5,429,734 A | * 7/1995 | Gajar et al. | 204/603 |
| 5,660,703 A | * 8/1997 | Dasgupta | 204/601 |

FOREIGN PATENT DOCUMENTS

EP 0816837 A1 * 7/1996
WO 9604547 2/1996

OTHER PUBLICATIONS

Fintschenko, Y. et al., "Glass Channels and Capillary Injectors for Capillary Zone Electrophoresis," *Sensor Technology in the Netherlands: State of the Art,* Kluwer Academic Publishers, Dordrecht, pp. 77–84, 1998.

* cited by examiner

Primary Examiner—A. Michael Chambers
(74) Attorney, Agent, or Firm—Webb Ziesenheim Logsdon Orkin & Hanson, P.C.

(57) ABSTRACT

The present invention relates to a device for controlling a liquid flow in a liquid channel, comprising: an elongate liquid holder in which a liquid channel is provided in longitudinal direction; first voltage means for applying a first voltage difference over substantially the longitudinal direction of the liquid channel; a conductor member arranged in at least a part of the liquid channel against the liquid holder; an insulator member arranged in the liquid channel against at least the conductor member; second voltage means for providing a second voltage difference between the conductor member and the liquid in the liquid channel; wherein the thickness of the insulator member is a maximum of 1 $\mu$m and preferably in the order of magnitude of some tens of nanometres.

19 Claims, 3 Drawing Sheets

DEVICE AND METHOD FOR CONTROLLING A LIQUID FLOW

BACKGROUND OF THE INVENTION

1. Field of the Invention

The present invention relates to a device for controlling a liquid flow in a liquid channel. The present invention also relates to an assembly and integrated circuit in which this device is placed, and to a method for manufacture thereof.

2. Description of the Prior Art

Charged particles in a solution or suspension of liquid channel con be transported by applying an electric field substantially parallel to the liquid channel. Under the influence of the electric field positively and negatively charged particles will move in opposing directions. This transport is also referred to as electrophoresis.

Another mechanism for generating a liquid flow in a liquid channel is formed by so-called electro-osmosis. The liquid channel is in this case enclosed by an electric insulator. At the location of the transition between the insulator and the liquid are situated charged insulator particles which are chemically bound to the insulator. As a consequence of the charge of these insulator particles, particles with an opposing charge are formed close to the insulator wall in the liquid channel. The layer consisting of the chemically bound insulator particles and the liquid particles charged in opposing directions is also referred to as the electric double layer. As a result of the presence of these particles with opposing charge, which are not chemically bound to the insulator, and the above mentioned electric field applied parallel to the direction of the liquid channel, a liquid flow will be generated along the walls of the liquid channel. The liquid flow along the walls brings about a liquid flow across the entire diameter of the liquid channel as a result of the friction between the liquid particles.

The moving charged particles define a shear plane at some distance of the insulator wall. The electrical potential at the location of this shear plane is called the $\zeta$-potential (Zeta potential). The magnitude of the $\zeta$-potential depends inter alia on factors such as the type of liquid or insulator, the concentrations of the different particles in the liquid, the pH value and the like. The direction and the degree of liquid flow resulting from electro-osmosis can be controlled by changing these factors.

It can be deemed known to vary the potential of the outer surface of the insulator with a voltage source, as a result of which the above stated $\zeta$-potential in the liquid channel can be varied. Since the direction and speed of the liquid flow in the liquid channel depends on the magnitude of the $\zeta$-potential, the movement of the particles in the liquid can be controlled with the voltage source, i.e. the movement of particles resulting from electrophoresis can be enhanced or decreased. While there are indeed devices known which enable such a control of the liquid flow in a liquid channel, they have large dimensions and require very high control voltages in the order of magnitude of several kVs, so that in practice they cannot be integrated with standard electronic components such as transistors, integrated circuits and so on.

The object of the present invention is to obviate these drawbacks.

SUMMARY OF THE INVENTION

According to an aspect of the invention, a device is provided for this purpose for controlling a liquid flow in a liquid channel, comprising:

an elongate liquid holder in which a liquid channel is provided in longitudinal direction;

first voltage means for applying a first voltage difference over substantially the longitudinal direction of the liquid channel;

a conductor member arranged in at least a part of the liquid channel against the liquid holder;

an insulator member arranged in the liquid channel against at least the conductor member;

second voltage means for providing a second voltage difference between the conductor member and the liquid in the liquid channel; wherein the thickness of the insulator member is a maximum of 1 µm and preferably in the order of magnitude of some tens of nanometres. In accordance with this aspect of the invention a device is therefore provided for controlling a liquid flow, wherein the functions of liquid container or liquid holder on the one hand and of insulator or $\zeta$-potential control layer on the other are separated, so that a great flexibility can be achieved in choice of material and method of manufacture.

According to a preferred embodiment of the invention the insulator member is formed from a thin layer or coating of insulator material, the conductor member and the liquid holder are combined and formed from a mechanically stable conductor material. The mechanically stable material provides in this case the required sturdiness of the device.

According to a further preferred embodiment of the invention the insulator member and the conductor member are formed from thin layers of respectively insulator material and conductor material, wherein the liquid holder is preferably formed from a mechanically stable material.

According to another aspect of the invention, a device is provided for controlling the liquid flow in a liquid channel, comprising:

an insulator member which defines an elongate liquid channel;

first voltage means for applying a first voltage difference over substantially the longitudinal direction of the liquid channel;

a conductor member arranged over at least a part of the outer surface of the insulator member;

second voltage means for providing a second voltage difference between the conductor member and the liquid in the liquid channel; wherein the distance between the outer surface and the inner surface of the insulator member is a maximum of 1 µm and preferably in the order of magnitude of some tens of nanometres. By making the wall thickness of the insulator member so small, the control of the liquid flow can advantageously be performed with a small second voltage difference, for instance with a voltage difference of less than 20 Volt. At such small wall thicknesses there moreover occurs a reduced loss of power and an improved heat discharge is possible.

According to a further preferred embodiment of the invention the device can be directly connected to standard electronic elements or integrated circuits or can even be integrated therewith. This preferred embodiment can therefore be advantageously connected directly onto and controlled by the output of the standard electronic elements such as integrated circuits, without additional provisions being required therein.

According to a further preferred embodiment of the invention the insulator member and the conductor member are manufactured from optically transparent materials. This has the advantage that the content and/or composition of the content of the liquid channel can be optically detected in simple manner.

According to a further preferred embodiment of the invention the insulator member is constructed from two or more insulator part-members manufactured with materials of different ζ-potential. This has the advantage that various flows with differing speeds and directions can be generated in the liquid channel without applying an external potential difference.

According to a further embodiment of the invention the insulator member is provided with two or more conductor members, to which mutually differing voltages can be applied. By applying different potentials to the conductor members, the associated ζ-potentials in the liquid channel will accordingly differ from each other. This has the advantage that different flows with differing speeds and/or directions of movement can be generated within the same liquid channel.

According to another preferred embodiment the voltage means comprise two electrodes which are arranged in the liquid channel. Because the electrodes can be arranged in the liquid the distance between the electrodes can be reduced, at least relative to the distance in the case of external electrodes, to an order of magnitude of a few-micrometers. Lower voltages are hereby sufficient to obtain the desired field strength of the electric field.

According to a further aspect of the invention, a system is provided for analysis and/or synthesis of chemical solutions or suspensions, wherein one or more of the above stated devices is used. According to a preferred embodiment of this system, this system comprises control means for controlling one or more liquids through a network of said devices.

According to a further preferred embodiment the network of said devices comprises one or more feed channels, two intermediate channels branched from the feed channels and one or more drain channels connected to the intermediate channels, wherein the intermediate channels are provided with gates which are supplied with voltage such that in the intermediate channels a substantially loop-like liquid flow results. Using such loop-like liquid flows the liquid in the intermediate channels can be circulated so that the liquid is mixed or enters into a chemical reaction.

According to a further aspect of the present invention, a pump system is provided for circulating liquid, in which preferably one or more of the above stated devices are used, comprising:

a liquid holder in which are provided a liquid feed channel and a liquid drain channel branched from the liquid feed channel;

first voltage means for applying an electric field in the longitudinal direction of the liquid feed channel;

a first and a second gate electrode which are placed on either side of the connection of the liquid drain channel to the liquid feed channel;

second voltage means for providing the first and second gate electrode with voltage;

control means for adjusting the first and second voltage means such that a pressure build-up occurs at the location of said connection and the liquid is drained via the liquid drain channel.

With the above stated system a pump can be realized on micro-scale, wherein the drain channel of the pump is voltage-free, this being advantageous since the drain channel can thereby be connected more easily to peripheral equipment and the like.

According to further embodiments of thee above stated pump system, the first voltage means generate an electric field alternately in a first and in a second, opposing direction in the liquid feed channel and the second voltage means, substantially synchronously with the first voltage means, switch the first gate electrode into enhancement mode and the second gate electrode into a reversement mode and vice versa. By circulating the liquid in such a manner polarization effects, such as the creation of air bubbles as a result of electrolysis, do not occur, which polarization effects could have an adverse effect on the operation of the pump.

According to a further aspect of the present invention, an electronic circuit is provided into which the above stated device is integrated.

According to a further aspect of the invention a method is provided for manufacturing the above stated device, comprising of:

etching a channel in a wafer;

depositing insulating material on the wafer;

manufacturing a glass plate;

anodic binding of the wafer on the glass plate;

etching the wafer; and fixing the conductor member.

By manufacturing the device in this manner liquid channels with the correct properties and very small wall thicknesses of a few tens of nanometres can be realized.

According to a further aspect of the present invention a method is provided for mixing two or more liquids, comprising of:

supplying the liquids via one or more liquid channels;

mixing the liquids by circulating the supplied liquid, preferably in the above stated system;

draining the liquids via one or more liquid drain channels.

BRIEF DESCRIPTION OF THE DRAWINGS

Further embodiments, advantages, features and details of the present invention will be elucidated in the following description with reference to the annexed figures, in which.

DETAILED DESCRIPTION OF THE PREFERRED EMBODIMENTS

Figure 1:
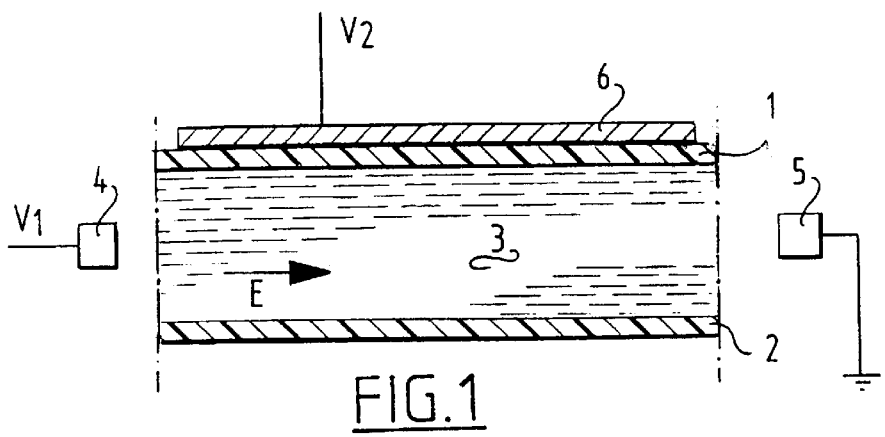
FIG. 1 shows a longitudinal section of a preferred embodiment of the invention.

Shown in the longitudinal section of FIG. 1 is a channel of rectangular cross-section, with an upper wall 1 and a lower wail 2 between which flows a liquid 3. Placed on the left-hand side of the channel is an anode 4 which is set to a voltage of $V_1$. Placed on the right-hand side of the liquid channel is a cathode 5 which is connected to the earth potential. As a result of the voltage difference between anode 4 and cathode 5 an electric field E is generated which transports positively charged particles in the direction of the arrow shown in the figure and negatively charged particles in the opposite direction (electrophoresis). The presence of positively or negatively charged particles in the liquid channel can be controlled by the choice of the insulator material of the insulator, the pH value of liquid 3, the concentration of the particles in the solution or suspension and so on. The presence of positively or negatively charged particles in the electrical double layer can however also be controlled using a conductor 6 which is arranged on the outside of insulator wall 1 and set to a voltage $V_2$.

Figures 2A, 2B:
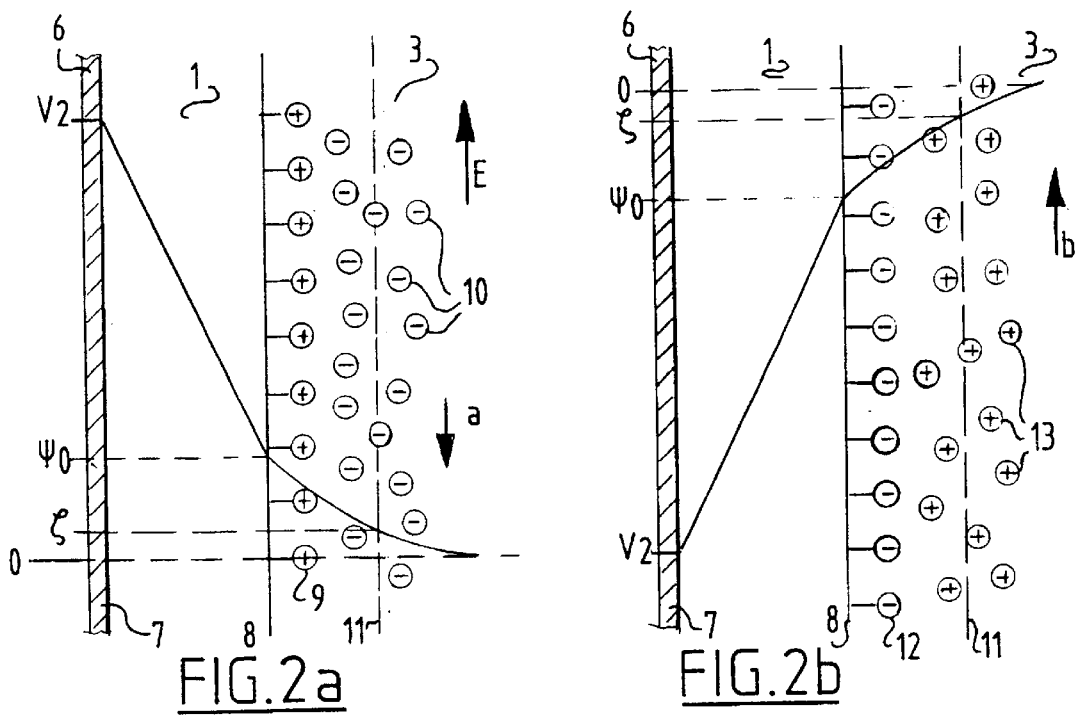
FIGS. 2a and 2b show schematic sketches of the operation of the electro-osmosis and electrophoresis mechanisms.

FIG. 2a shows the progression of the positive voltage applied to the insulator wall by conductor 6. On the interface 7 between conductor 6 and wall 1 the voltage equals $V_2$, while the voltage decreases as the interface between wall 1 and liquid 3 is approached. At the location of interface 8 the voltage has a value $\psi_0$, which voltage is designated as the wall potential. The wall potential is the consequence of charged particles 9, in this case positively charged particles, chemically bound to wall 1. Negatively charged particles 10 will occur in the liquid to compensate herefor. The voltage in the liquid channel decreases further as the distance from interface 8 increases. As a result of the applied field E the non-bound negatively charged particles 10 will be subjected to a force in the direction of the arrow a. This electric force decreases as the distance from the wall surface increases, since the number of negatively charged particles in this direction decreases. As a result of this electric force the part of the liquid in the electric double layer to the left of the shear plane or inner Helmholtz plane 11 will therefore start to move parallel to the wall surface, while the remaining part of the liquid is co-displaced by friction.

Shown in FIG. 2b is the situation where the voltage $V_2$ on conductor 6 is negative, so that the wall potential $\psi_0$ is negative. There therefore results in the electric double layer, in addition to the chemically bound negative charges 12, a quantity of positively charged particles 13 which are transported in the direction of arrow b as a result of the electric field E which is present.

The liquid channels can be manufactured according to a method as described in the article "Glass channels and capillary injectors for capillary zone electrophoresis", pages 77–84, Y. Fintschenko et al, in: A van de Berg en P. Bergveld, "Sensor Technology in the Netherlands: State of the Art", Kluwer Academic Publishers, Dordrecht, 1998, pages 77–84. As alternative to this method of manufacture the devices according to the invention can be manufactured with a so-called "Self-Assembled Mono-layer" (SAM layer) on gold, silver or Si. A monolayer of thioalkanes for instance (which form a very good and thin insulator) is herein coated from the inside on a hollow Au pipe. A sulphur group S is herein bound on the inside of the Au pipe in chemical manner, which group is connected via hydrophobic hydrocarbon chains to a functional end group, which end group influences the ζ-potential. The total thickness of the SAM layer is about 0.5–10 nm. Alternative manufacturing methods can also be envisaged in addition to the above described methods of manufacture.

By in any case embodying the liquid channels in this manner very thin wall thicknesses of less than 1 μm, preferably in the order of magnitude of a few (tens of) nanometres can be realized. As a result of these small dimensions the required magnitude of the control voltage $V_2$ is very low, for instance a few mV or V, and generally a maximum of 20 Volt. It is hereby possible to influence the liquid flow with relatively low voltages, wherein use can therefore be made in practice of the voltages occurring in standard electronic components such as transistors, integrated circuits and so on. An improved heat discharge can also be realized due to the small wall thickness. Relative to known liquid channels, which have a wall thickness of about 100 μm, the heat discharge is for instance up to four times faster.

Figure 3:
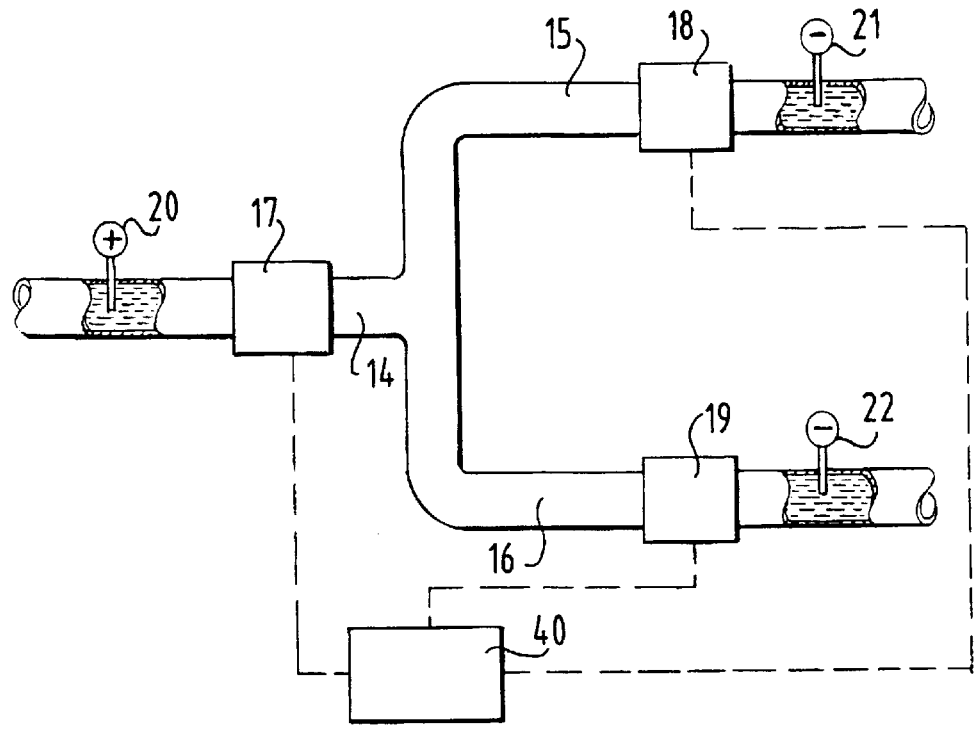
FIG. 3 is a schematic perspective view of another preferred embodiment of the invention, in which a network of liquid channels forms an electrical switch.

FIG. 3 shows a view of a preferred embodiment of the invention, in which an electrical switch is formed in a network of liquid channels. A liquid channel 14 branches at a given position into two liquid channels 15 and 16. Between the beginning of liquid channel 14 and the ends of liquid channels 15 and 16 a potential difference is applied by means of an anode 20 and two cathodes 21 and 22. As a result of this voltage difference a flow occurs in liquid channel 14 in the direction of the arrow shown in FIG. 3. In order to create an electrical switch with which the flow can be divided over the two liquid channels 15 and 16 at the branching, a conductor 17 is arranged on liquid channel 14, a conductor 18 on liquid channel 15 and a conductor 19 on a liquid channel 16. By supplying conductors 17, 18 and 19 with suitable voltages, the associated potentials are adjusted and the liquid flow in the network of channels can be controlled. Shown in table I is an overview of the voltage values required to control the direction of the liquid flow. This shows that for flow from channel 14 to channel 15 the voltage $V_{17}$ on conductor 14 must be positive, the voltage $V_{18}$ on conductor 15 must be positive and the voltage $V_{19}$ on conductor 16 must be negative. For flow from channel 14 to channel 16 the voltage $V_{17}$ on conductor 14 must be positive, the voltage $V_{18}$ on conductor 15 must be negative and the voltage $V_{19}$ on conductor 16 must be positive.

TABLE I

|  | 14 → 15 | 14 → 16 |
|---|---|---|
| $V_{17}$ | + | + |
| $V_{18}$ | + | − |
| $V_{19}$ | − | + |

Figure 4:
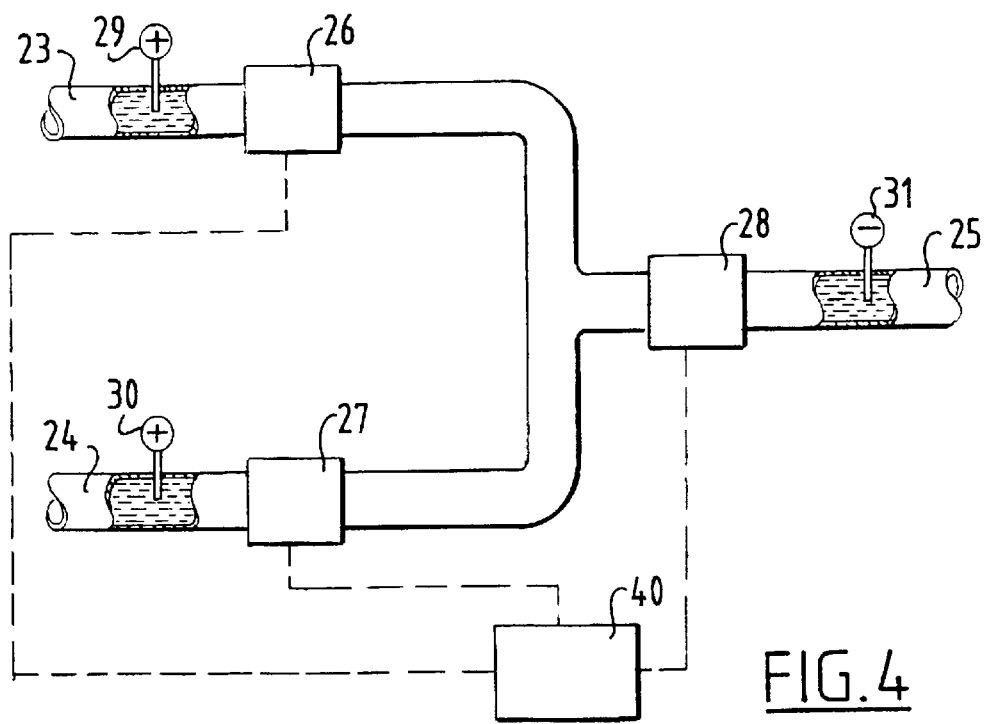
FIG. 4 shows a schematic perspective view of another preferred embodiment of the invention, depicting another electrical switch.

FIG. 4 shows an alternative electrical switch wherein the infeed consists of a channel 23 and a channel 24 and the outfeed consists of a channel 25, which either transports the liquid out of channel 23 or the liquid out of channel 24. Anodes 29 and 30 are placed at the beginning of liquid channels 23 and 24, while a cathode 31 is placed at the end of liquid channel 25. By applying a voltage difference hereover an electric field is created in the liquid. Conductors 26 and 27 are moreover arranged on respectively liquid channel 23 and liquid channel 24 and a conductor 28 is arranged on liquid channel 25. Table II shows the voltage values required to control the direction of the liquid flows. This shows that when the liquid flow of channel 23 has to be drained via channel 25, the voltage $V_{26}$ on conductor 26 must be positive, the voltage $V_{27}$ on conductor 27 must be negative and the voltage $V_{25}$ on conductor 25 must be positive. If on the other hand the liquid from liquid channel 24 must be drained through liquid channel 25, the voltage $V_{26}$ on conductor 26 must be negative, the voltage $V_{27}$ on conductor 27 must be positive and the voltage $V_{28}$ on conductor 28 must be positive.

TABLE II

|  | 23 → 25 | 24 → 25 |
|---|---|---|
| $V_{26}$ | + | − |
| $V_{27}$ | − | + |
| $V_{28}$ | + | + |

FIGS. 3 and 4 show that conductors 17, 18, 19, 26, 27, 28 are preferably connected to a central control 40 in order to control the direction and speed of the liquid flows in the network of liquid channels.

In an embodiment of the invention which is not shown, a large number of electrical switches according to FIGS. 3 and 4 connected in parallel or in series can be combined to an extensive network of liquid channels in which the flow of the liquid can be regulated by a central control.

Figure 5:
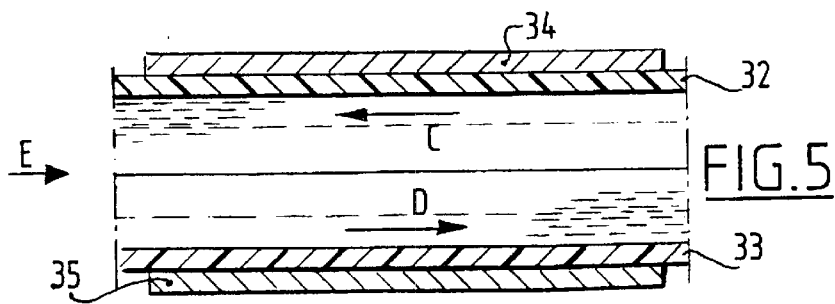
FIG. 5 shows a longitudinal section of another preferred embodiment of the invention.

FIG. 5 shows a liquid channel wherein on the upper side of the channel the insulator 32 is manufactured from a first material, while on the underside the insulator 33 is manufactured from a second material, wherein the first and second materials have different ζ-potentials. It is also possible to arrange a conductor 34 on the top side of insulator 32, while a second conductor 35 is arranged against the underside of the bottom insulator 31. If different voltage values are applied to conductors 34 and 35, different ζ-potentials occur in the liquid. When the voltage on conductor 34 is for instance positive, while the voltage on conductor 35 is negative, the liquid in the vicinity of the upper wall will move in the direction of arrow C and the liquid in the vicinity of the bottom wall will move in the direction of arrow D. It is hereby possible to bring about different directions of movement of the liquid in one channel, which may for instance be important when separating compositions.

The most important field of application of the present invention is in the development of new medicines and bio-analysis. Large numbers of substances must herein be analyzed very quickly, at a speed of for instance more than 10,000 analyses per hour. Another important field of application of the present invention is so-called "fluid-chemical computing" or "DNA-computing", as for instance described in "computing with DNA" by L. M. Adleman, Scientific American, August 1998, page 34–41. A determined liquid volume in the liquid channel according to the invention, for instance with dimensions of $10 \ \mu m * 1 \ \mu m * 1 \ \mu m$, can easily contain $10^3$ DNA molecules, or $10^{12}$ bits or information. Control of the liquid flow in the liquid channel as set out above with a switching time of 1 $\mu s$ yields a data transfer speed of $10^{18}$ bits/s, which is much faster than the data transfer speed in the present electronics.

Figure 6:
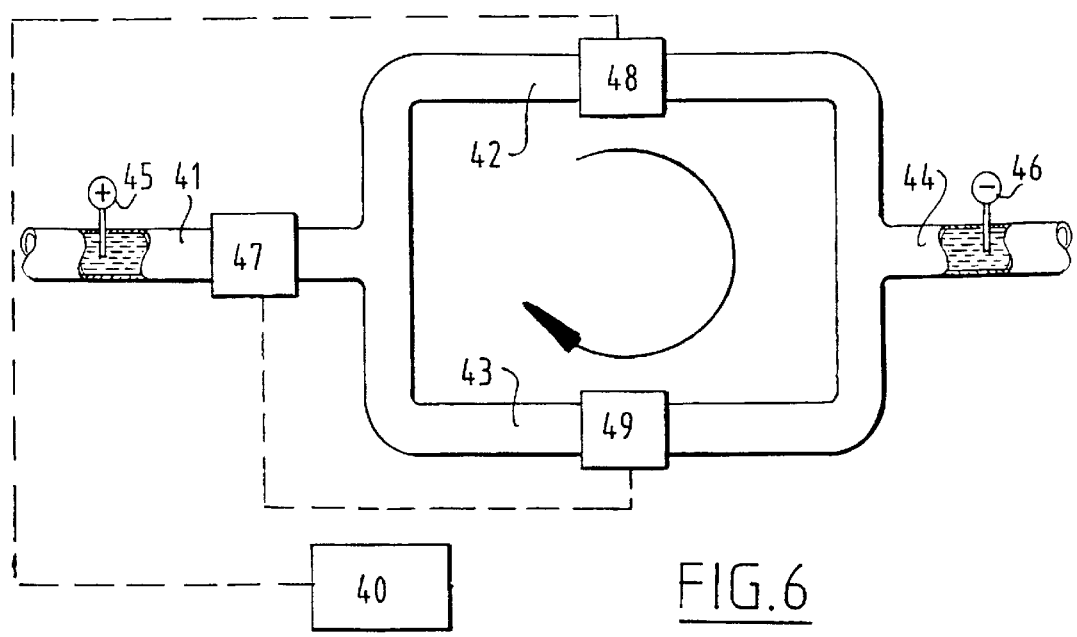
FIG. 6 shows a schematic view of a further preferred embodiment of the invention for applications in a bioreactor.

FIG. 6 shows a schematic view of an application of the invention on a pump for circulating and mixing liquids in bioreactor applications. Use is made herein of a circuit of two flow channels in a so-called twin channel network. FIG. 6 shows that a liquid is fed via channel 41, which channel 41 subsequently branches into a channel 42 and a channel 43. Channels 42 and 43 join together again a little further along in drain channel 44. Using anode 45 and cathode 46 an electric field, which in the example of FIG. 6 is directed substantially from left to right, is generated in the channels. Liquid channels 41, 42 and 43 are respectively provided with conductors 47, 48 and 49. Using conductor 47 the liquid is fed in a manner already described with reference to FIG. 3. By then providing conductors 48 and 49 with suitable voltages, i.e. conductor 48 such that an enhancement mode is generated and conductor 49 such that a reversement mode is generated, the liquid in liquid channels 42 and 43 is circulated in a clockwise direction, which is indicated in the figure with an arrow. By providing conductors (gates) 48 and 49 with voltage such that in channel 42 the reversement mode and in channel 43 the enhancement mode prevails, the rotation direction of the liquid flow can be reversed. With above stated (twin channel) network liquids can be fed in simple manner and subsequently mixed during circulation. It is also possible to have different liquids react with each other during circulation. Control of gates 48 and 49 (and 47) preferably takes place by means of a central control 40 so that the direction and speed of the liquid flows in the network of liquid channels is easy to control. After the liquid has been circulated sufficiently, gates 48 and 49 are both switched into the enhancement mode whereby the liquid can be drained via liquid channel 44. It is noted that the above stated circulation can also be implemented in other ways. Conductor 47 for instance may thus be omitted as the case requires, or an extra conductor may be added in drain channel 44. It is also possible to place anode and cathode 45 and 47 at other positions or to provide each conductor (gate) 47, 48, 49 with its own anode-cathode pair, for instance in a manner as occurs in a preferred embodiment discussed herein below.

Figure 7:
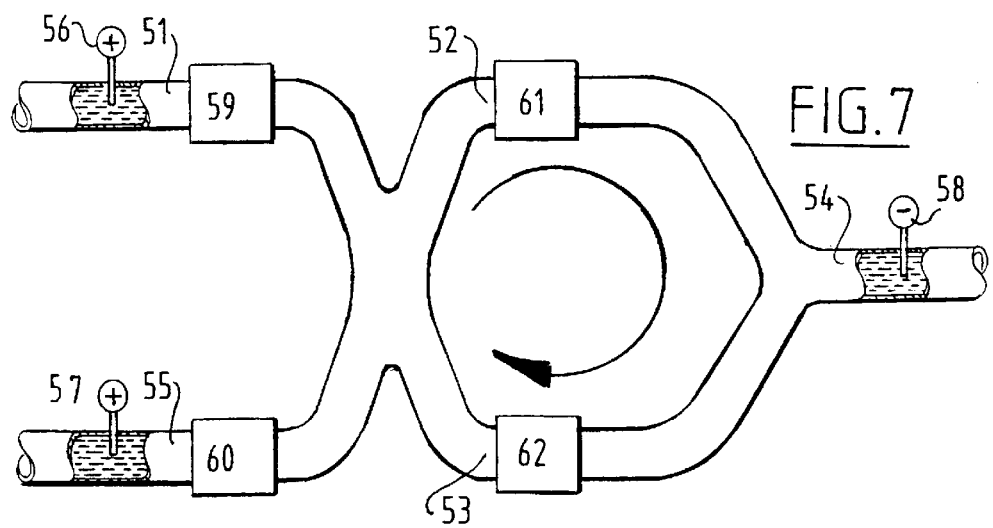
FIG. 7 shows a schematic view of a further preferred embodiment for applications in a bioreactor.

FIG. 7 shows another advantageous embodiment, in which liquid is fed via two different liquid channels 51 and 55 into a twin channel network consisting of an upper liquid channel 52 and a lower liquid channel 53, and the liquid is drained in drain channel 54 in a manner corresponding wholly with the embodiments of FIG. 6. Using anodes 56 and 57 and cathode 58 an electric field is generated in the channel system. Through a suitable switching of gates 59, 60, 61 and 62 associated with respective liquid channels 51, 55, 52 and 53, the different liquids can be fed via the associated feed channels 51 and 55 in adjustable ratios and can be mixed with each other through being pumped round in channels 52 and 53, wherein a chemical reaction may occur. When for instance a first component is fed via liquid channels 51 and a second component via liquid channel 55, a reaction between the two components can take place during pumping of the two liquids round liquid channels 52 and 53. Depending on the set voltages, the mixing ratio of substances fed via channel 51 and channel 55 can be adapted as desired. At a desired moment, for instance when a reaction between -the two liquids has ended, the liquids which have reacted with each other are drained via drain channel 54 also referred to as drain. The above stated mixing ration depends on the feeding speeds in liquid channels 51 and 55 and the volumes in the channels. In addition to being used for a continuous supply of different liquids, the network can also be used in applications in which processes have to be performed batchwise.

It is noted that additional branches of the twin channel network can be connected as desired in order to allow further different components into the circuit.

It is important to adjust the voltages on the gates such that the maximum circulation takes place while the hold-up, i.e. the mixing ratio between the liquids, is optimal.

Figures 8, 9A, 9B:
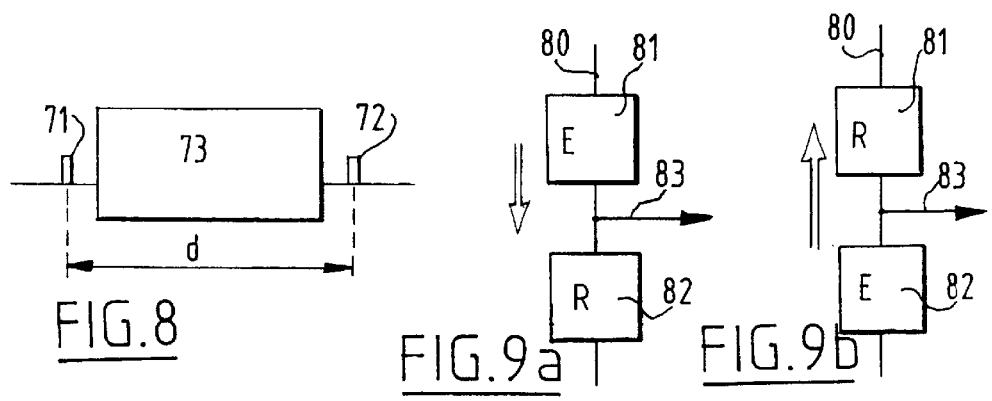
FIG. 8 is a schematic view of a further preferred embodiment for applications as pump.
FIGS. 9a and 9b are schematic views of another preferred embodiment of a pump.

FIGS. 9a and 9b show another embodiment of a pump. FIG. 9a shows in schematic manner a channel 80 which is provided with the branch 83. Channel 80 is provided with a gate 81 and a gate 82. In a manner as described in the foregoing embodiments, an electric field is generated in channel 80 in the direction of the double arrow. By switching gate 81 into the enhancement mode E and gate 82 into the reversement mode R, a pressure build-up is created in channel 80 such that the liquid is carried into the side channel 83 and is drained via this side channel. The advantage of this manner of pumping is that no electric field is hereby present in channel 83, or channel 83 is hereby voltage-free. As a result hereof the drain of such a pump can be connected more easily onto external equipment.

FIG. 9b shows a situation in which a similar pumping action is brought about in side branch 83, with the difference that the electric field is now directed from bottom to top and gates 81 and 82 are switched in opposing directions, i.e. gate 81 is switched into the reversement mode R and gate 82 into the enhancement mode E. In this configuration the liquid from above is also urged via tube 80 into side tube 83 whereby the channel system functions as pump. By now alternating the situations shown in FIGS. 9a and 9b with a suitable frequency, i.e. reversing the electric field and reversing the switching mode of gates 81 and, 82, no polarization effects will occur on the electrodes in the case of a substantially continuous pumping action. The term "polarization effects" refers to the adverse effects which can for instance cause electrolysis in water, whereby gas bubbles occur in the liquid channels and the pumping action is greatly reduced.

FIG. 8 shows a further preferred embodiment of a pump. Channel 70 is provided with a gate electrode 73. Arranged on either side of gate electrodes 73 are metal electrodes 71 and 72 with which an electric field can be generated. By applying the electric field between electrodes 71 and 72 an electro-osmotic flow can be created which is influenced by the voltage of gate electrode 73.

By providing electrodes 71 and 72 with alternating voltage there would indeed be no occurrence of polarization effects such as formation of gas bubbles if the voltage of gate electrodes 73 remained constant, but the liquid in the channel is not displaced either. By also switching gate electrode 73 substantially synchronously with alternating of the voltage of electrodes 71 and 72, a liquid flow can still be generated in channel 70 without polarization effects occurring.

In this embodiment the gate electrodes 71 and 72 are integrated in the tube and. (external) electrodes outside the channel can be omitted. This not only has the advantage that such a channel 70 can be connected directly onto external peripherals, but also has the advantage that much lower voltages can be used since the distance d between electrodes 71 and 72 can be much smaller than in the case where the electrodes are arranged externally. Since the distance d is in the order of magnitude of a few micrometers, a pump of extremely small dimensions can be realized.

The above stated invention can be applied not only on aqueous media but also on non-aqueous media such as for instance alcohol, methanol, THF, DMSO or any other random solvents. It may be necessary herein to dissolve organic salts in the medium to ensure a sufficient degree of conductivity.

The present invention is not limited to the above described preferred embodiment thereof; the rights sought are defined by the following claims, within the scope of which many modifications can be envisaged.

What is claimed is:

1. A device for controlling the electro-osmotic flow of a liquid in a liquid channel, said device comprising:
    a) an insulator member provided with an elongate liquid channel;
    b) a first voltage means comprising a first electrode and a second electrode for applying a first voltage difference over substantially the longitudinal direction of the liquid channel to provide an electric field in the liquid channel;
    c) a conductor member arranged between the first and second electrode on at least a part of the outer surface of the insulator member; and
    d) a second voltage supply means connected to the conductor member for providing a second voltage difference between the conductor member and the liquid in the liquid channel so as to control the electro-osmotic flow of the liquid in the liquid channel, wherein:
    the insulator member is fabricated with a thickness of a maximum of 1 $\mu$m;
    the second voltage difference is a maximum of 20 V;
    the first voltage means generates an electric field alternately in a first direction and in a second direction, opposite the first direction, in the liquid channel; and
    the second voltage supply means switches substantially synchronously with the alternating electric field.

2. The device as claimed in claim 1, wherein the first voltage means and the second voltage supply means are directly connectable to and controllable by standard electronic elements or integrated circuits.

3. The device as claimed in claim 1, wherein the insulator member comprises a coating arranged on the conductor member, which is formed from a mechanically stable, supporting conductor material.

4. The device as claimed in claim 1, wherein both the insulator member and the conductor member are coatings arranged on a mechanically supporting material.

5. The device as claimed in claim 1, wherein the distance between the outer surface and the inner surface of the insulator member is in the order of magnitude of some tens of nanometres.

6. The device as claimed in claim 1, wherein the insulator member and the conductor member are manufactured of optically transparent.

7. The device as claimed in claim 1, wherein the insulator member is constructed from two or more insulator part-members, each of different Zeta-potential.

8. The device as claimed in claim 1, wherein two or more conductor members, to which differing voltages can be applied, are fixed to an insulator member.

9. The device as claimed in claim 1, wherein the liquid channel has a substantially rectangular cross-section.

10. The device as claimed in claim 1, wherein the liquid channel has a substantially round or semi-round cross-section.

11. The device as claimed in claim 1, wherein the first voltage means comprise two electrodes which are arranged in the liquid channel.

12. The device as claimed in claim 9, wherein the distance between the electrodes is in the order of magnitude of a few micrometers.

13. A method for manufacturing the device as claimed in claim 1, a device for controlling electro-osmotic flow of a liquid in a liquid channel, the method comprising the steps of:
    etching a channel in a wafer;
    depositing insulator material on the wafer;
    manufacturing a glass plate;
    anodic binding of the wafer on the glass plate;
    etching the wafer; and
    fixing a conductor member on the insulator material.

14. A system for analysis and/or synthesis of chemical solutions or suspensions, the system comprising:
    at least one fluid feed channel having a gate electrode;
    at least one fluid drain channel;

a pair of intermediate fluid channels connected in parallel fluid communication between each fluid feed channel and each fluid drain channel, each intermediate fluid channel including a gate electrode;

first means for applying an electrical potential across fluid received in each fluid feed channel, each fluid drain channel and the intermediate fluid channels; and second means for applying an electrical potential to the gate electrodes of each fluid feed channel and the intermediate fluid channels concurrent with the electrical potential applied across the fluid received in each fluid feed channel, each fluid drain channel and the intermediate fluid channels, wherein the second means for applying the electrical potential applies electrical potentials to the gate electrodes which cause the fluid received in the intermediate fluid channels to circulate therein.

15. The system as claimed in claim 14, wherein the fluid circulates in the intermediate fluid channels in one of a first direction and a second direction opposite the first direction.

16. The system as claimed in claim 14, wherein the means for applying electrical potentials applies electrical potentials to the gate electrodes which cause the fluid to drain through the at least one fluid drain channel.

17. A pump system for controlling a flow of liquid supplied via a first channel to a junction formed by the intersection of the first channel with a second channel and a third channel, the pump system comprising:

a first gate electrode arranged on the first channel;

a second gate electrode arranged on the second channel;

first means for applying an electrical potential across fluid received between the first channel and the second channel; and second means for applying an electrical potential to the first and second gate electrodes concurrent with the application of the electrical potential across the fluid received between the first channel and the second channel whereupon a pressure of the fluid between the first and second gate electrodes increases and urges the fluid received therebetween toward the third channel.

18. The pump system as set forth in claim 17, wherein the first and second gate electrodes are responsive to the second means for applying the electrical potential thereto for operating in an enhancement mode and a reversement mode, respectively, to increase the pressure of the fluid between the first and second gate electrodes.

19. The pump system as set forth in claim 18, wherein:

the first means for applying the electrical potential across the fluid received between the first channel and the second channel applies the electrical potential alternately in a first and a second, opposing direction; and the second means for applying the electrical potential to the first and second gate electrodes switches the first and the second gate electrodes, substantially synchronously with the alternating potential, between the enhancement mode and the reversement mode.

* * * * *

UNITED STATES PATENT AND TRADEMARK OFFICE
CERTIFICATE OF CORRECTION

PATENT NO. : 6,508,273 B1
DATED : January 21, 2003
INVENTOR(S) : Albert Van Den Berg It is certified that error appears in the above-identified patent and that said Letters Patent is hereby corrected as shown below:

Column 1,
Line 13, "channel con be" should read -- channel can be --.

Column 4,
Line 1, "of thee" should read -- of the --.

Column 7,
Line 47, "bits or information" should read -- bits of information --.

Column 8,
Line 45, "between -the" should read -- between the -- (delete hyphen).

Column 9,
Line 39, "and. (external)" should read -- and (external) -- (delete period).

Column 10,
Line 35, "transparent." shold read -- transparent materials. --.

Signed and Sealed this

Sixth Day of May, 2003

JAMES E. ROGAN
*Director of the United States Patent and Trademark Office*